United States Patent
Ustuner

(10) Patent No.: US 8,245,577 B2
(45) Date of Patent: Aug. 21, 2012

(54) PULSE PERIOD JITTER FOR ARTIFACT DETECTION OR REDUCTION IN ULTRASOUND IMAGING

(75) Inventor: Kutay F. Ustuner, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 494 days.

(21) Appl. No.: 12/499,690

(22) Filed: Jul. 8, 2009

(65) Prior Publication Data
US 2011/0005322 A1  Jan. 13, 2011

(51) Int. Cl.
*G01N 29/00* (2006.01)
(52) U.S. Cl. ............................................ 73/627; 73/641
(58) Field of Classification Search ............. 73/627, 73/592, 641, 633; 600/441, 453–455, 447, 600/437–438
See application file for complete search history.

(56) References Cited

U.S. PATENT DOCUMENTS

| | | | | |
|---|---|---|---|---|
| 4,182,173 | A * | 1/1980 | Papadofrangakis et al. | 73/861.27 |
| 4,851,853 | A * | 7/1989 | Mahoney | 342/174 |
| 5,617,863 | A * | 4/1997 | Roundhill et al. | 600/447 |
| 6,150,976 | A * | 11/2000 | Cooley | 342/169 |
| 2006/0064018 | A1 | 3/2006 | Chomas | |
| 2007/0066896 | A1* | 3/2007 | Simopoulos et al. | 600/437 |
| 2007/0083109 | A1* | 4/2007 | Ustuner et al. | 600/437 |
| 2009/0306513 | A1* | 12/2009 | Srinivasan et al. | 600/454 |
| 2010/0022884 | A1* | 1/2010 | Ustuner et al. | 600/453 |

* cited by examiner

*Primary Examiner* — Helen C. Kwok

(57) ABSTRACT

Depth ambiguity artifact is addressed. The pulse repetition interval is periodically varied. This jitter in the interval causes variance in the artifact while maintaining actual tissue or signal. The variation of the artifact may be visually detected or automatically detected and reduced, such as by removal. By removing the information associated with the variation of the artifact, the constant or maintained information may be presented with fewer artifacts. The variation may result in greater blurring of the artifact thereby reducing the artifact.

20 Claims, 2 Drawing Sheets

PULSE PERIOD JITTER FOR ARTIFACT DETECTION OR REDUCTION IN ULTRASOUND IMAGING

BACKGROUND

This present document relates to depth ambiguity artifact in ultrasound or pulse-echo imaging. If the pulse repetition interval (PRI) is not long enough to let the previous pulse attenuate sufficiently before firing the next pulse, echoes from deep echogenic objects interfere with the echoes from shallower objects. This creates images of deeper objects superimposed on the image of shallower objects. Such artifacts are known as depth ambiguity artifacts.

These artifacts are undesired, particularly for pelvic, OB and cardiac exams where the signal path includes low attenuation anechoic or hypo-echoic chambers. These chambers are displayed as black or uniform regions. However, the artifacts may be superimposed on the chamber region, resulting in an image showing tissue in a region without tissue.

A previous ultrasound imaging system allowed the user to manually verify the existence of depth ambiguity artifacts. A "Frame Rate" function allowed the user to increase the pulse repetition interval by 50%. This change in pulse repetition interval would slow the frame rate, but shift the location of any depth ambiguity artifacts. The user could then determine whether a structure in the image was an artifact from a deeper tissue. If the structure in the image moves to a different depth upon toggling the Frame Rate, the structure is an artifact. However, the slowed frame rate is not desired. Merely shifting the artifact still results in the artifact being in the image. Manual toggling requires effort by sonographers already very busy performing an ultrasound exam.

BRIEF SUMMARY

By way of introduction, the preferred embodiments described below include methods, systems, computer readable media, and instructions for addressing depth ambiguity artifact. The pulse repetition interval is periodically varied. This jitter in the interval causes variance in the artifact while not causing variance in actual tissue or signal from the appropriate depths. The variation of the artifacts may be visually detected or automatically detected and reduced, such as by removal. By removing the information associated with the variation of the artifact, the constant or maintained information may be presented with fewer artifacts. The variation alone may result in greater blurring of the artifact, reducing the artifact.

In a first aspect, a method is provided for addressing depth ambiguity artifact in ultrasound imaging. A series of pulses are transmitted from a transducer. The pulses of the series are separated in time by a pulse repetition interval. The pulse repetition interval periodically varies within the series such that an amount of time between the pulses increases after about N pulses and decreases after about N pulses. Acoustic echoes are received in response to the pulses. An image is generated as a function of the received acoustic echoes. The image is associated with the depth ambiguity artifact addressed as a function of the varying.

In a second aspect, a computer readable storage medium has stored therein data representing instructions executable by a programmed processor for addressing depth ambiguity artifact in ultrasound imaging. The storage medium includes instructions for pulse-echo imaging of an object, jittering a pulse period in the pulse-echo imaging, and reducing the artifact in the pulse-echo imaging as a function of the jittering.

In a third aspect, a system for addressing depth ambiguity artifact is provided in ultrasound imaging. A transmit beamformer is configured to transmit beams for a same imaging mode with a repetition interval between successive ones of the beams. The repetition interval regularly varies other than caused by any interleaving between imaging modes. A receive beamformer is configured to receive beams in response to the transmitted beams. An image processor is configured to generate an image from the received beams.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Introducing a jitter to the pulse period may help automatically detect, locate, reduce or eliminate the depth ambiguity artifact. The pulse period jitter shifts the artifact depth while signal (i.e., information from structure at the imaged depth) remains stationary. This allows detection of the presence of artifact and enables automatic reduction or elimination of the artifact using pre-detection or post-detection processing. The jitter may be periodic with a periodicity of N pulse repetition intervals, or N frame/volume periods, where N>1. The jitter amount may be as small as Tc/2, where Tc=1/fc and fc is the imaging center frequency at deepest depth of an imaging region. The jitter amount may be larger than the axial resolution to introduce a visible shift (and jitter) to the artifact.

In one embodiment of pulse-echo imaging, the pulse period has a jitter. The artifact may be addressed using the jitter. Receive beams from successive firings are filtered by a filter prior to intensity detection. The filtering removes or reduces the artifact due to the higher frequency shift caused by the jitter.

Figure 1:
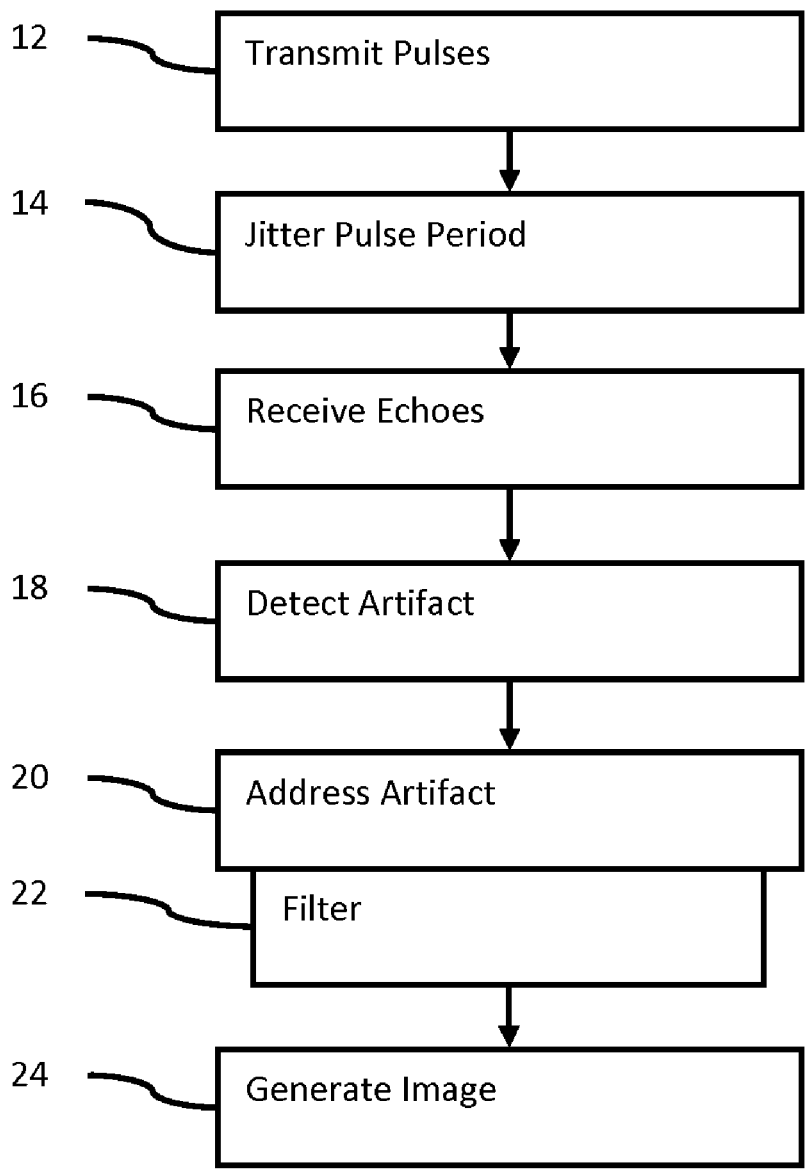
FIG. 1 is a flow chart diagram of one embodiment of a method for addressing depth ambiguity artifact in ultrasound imaging.

FIG. 1 shows a method for reducing depth ambiguity artifact in ultrasound imaging. The method is performed in the order shown, but other orders may be used. Additional, different, or fewer acts may be performed. For example, act 18 is not performed. Instead, an image is generated or the artifact is reduced without specific detection of the artifact. As another example, acts 20 and 22 are not performed.

Transmission in act 12, reception in act 14, and generation of the image in act 24 provide pulse-echo imaging. Pulses are transmitted as acoustic beams, echoes are generated in response to the pulses, receive beams are formed from the echoes, and an image is generated from the receive beams. Sequential transmit beams and corresponding receive beams are formed along different scan lines to scan a region of a patient or other object. In other embodiments, the pulse period is jittered for processing of information without imaging.

In act 12, pulses are transmitted. Electrical waveforms are generated for each element within a transmit aperture. The waveforms are unipolar, bipolar, sinusoidal, or other waveforms. The waveforms are of a short duration, such as 1-10 cycles. Longer duration waveforms may be used, such as associated with coded transmit waveforms (e.g., chirp or frequency coded waveforms). The waveforms are centered at an imaging frequency, such as 2-10 MHz. The waveforms may be centered at a different frequency. For example, the waveforms are centered at 2 MHz for imaging at the second harmonic centered at 4 MHz.

The waveforms are relatively delayed and apodized. The relative delays and apodization shape a beam. The waveforms are applied to a transducer. The elements of the transducer generate acoustic energy in response to the electrical waveforms. The acoustic energy coherently combines along one or more scan lines as a transmit beam. The beam may be focused within a region of interest, focused outside the region of interest (e.g., infinite focus of a plane wave) or defocused (e.g., diverging wave front). The transmit beam may have any width, such as a transmit beam covering a plurality of receive scan lines. Waveforms may be combined to transmit along multiple scan lines simultaneously, providing simultaneous transmit beams.

A series of pulses are transmitted. Successive transmit beams are generated from the transducer. The transmit beams are formed at the same location or different locations. For example, the transmit beams are sequentially transmitted along different scan lines to scan a two-dimensional region and/or a volume of a patient.

The series of pulses are for one type of imaging, such as B-mode, M-mode, color mode, F-mode (flow mode), or any other now known or later developed type of ultrasound imaging. The pulses for one mode may be interleaved with pulses for another mode. For example, a region is scanned for B-mode. Before repeating the B-mode scan, pulses for flow mode or velocity estimation are transmitted. As an alternative to frame or volume interleaving, the interleaving may be by line or group of lines.

The pulses are separated in time by a pulse repetition interval (PRI). The PRI is set to a time for the acoustic energy to travel to a deepest imaging depth and responsive echoes to return from the depth or greater time. The PRI is set to longer than the two-way acoustic travel time to allow any echoes from deeper, non-imaging depths, to pass without detection or attenuate. Depending on the signal strength and reception sensitivity, such echoes may cause depth ambiguity artifacts. Removing the artifact by an increased PRI may undesirably slow the rate of scanning.

The PRI may vary between modes of imaging. For example, the PRI for B-mode may be different from the PRI for flow or tissue motion imaging. Due to interleaving pulses for different modes, the PRI may vary for a given mode. For example, the PRI may be X for B-mode. Due to interleaving of Doppler pulses, the PRI between two of the pulses for B-mode is greatly longer to allow transmission of the Doppler pulses.

Figure 2:
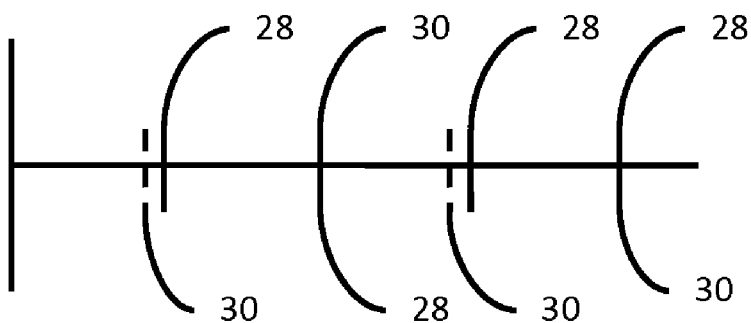
FIG. 2 is a graph showing jittering of the pulse repetition interval.
Figure 3:
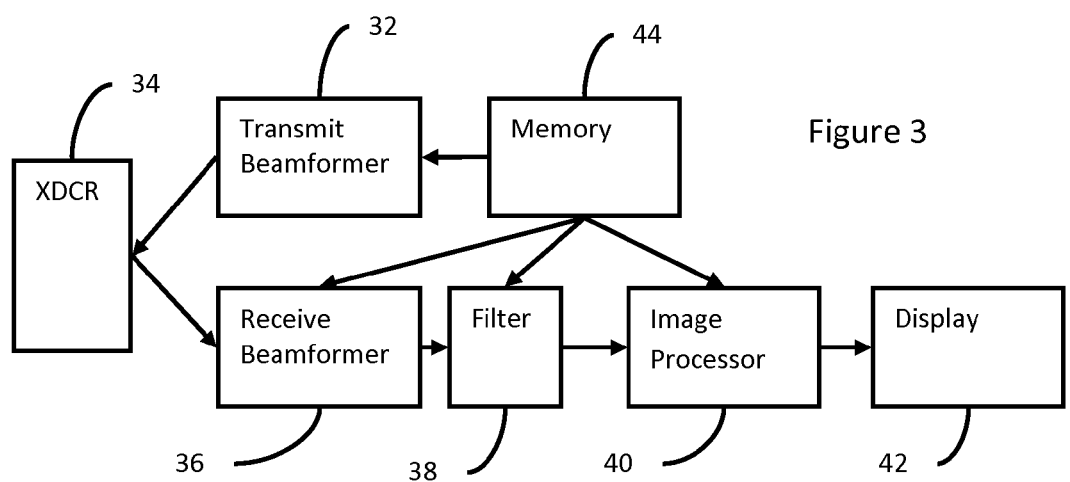
FIG. 3 is a block diagram of one embodiment of a system for addressing depth ambiguity artifact is provided in ultrasound imaging.

In act 14, the pulse period is jittered in the pulse-echo imaging. The jitter is in addition to any variation caused by interleaving of pulses for different modes. FIG. 2 shows a sequence of transmit events with equal PRI at 28. Dashed lines at 30 show variation in the PRI associated with jitter. The base PRI is the same, so some of the transmit events occur at a same time. Due to the jitter, some of the transmit events shown at 30 occur at a different time than for the transmit events shown at 28.

Jitter is a time variation in the pulse period. The jitter is periodic, such that the pulse repetition interval periodically varies within the series of pulses. Other regular or irregular variation in the PRI may be used. For example, the PRI is coded. The jitter results in different amounts of time between different pairs of pulses. The amount of time between two pulses may increase, and then the amount of time between another two pulses may decrease. The jitter has a period associated with an increase and a decrease. The periodic variation is repeated each period, causing the PRI to regularly vary.

A jitter $\Delta T$ is added to the pulse period T. The jitter may help automatically locate, reduce or eliminate the depth ambiguity artifact without or with less decrease in the frame or scan rate than without the jitter. Let $s_i(t)$ be the echo in response to the $i^{th}$ pulse/echo event (transmit and responsive receive). If there is a target at depth d, there is an echo $T_d$ seconds later, where $T_d=2d/c$, and c is the speed of sound. If the target is represented as a delta function, the echo is:

$$s_i(t)=h(t-Td)$$

where h(t) is the round trip impulse response of the imaging system. For simplicity, the effects of beamforming are not considered.

If the pulse repetition interval T is less than $T_d$, then the echo in response to $(i+1)^{st}$ pulse/echo event is superimposed with an echo from the $i^{th}$ pulse/echo event. In the case where the lateral beam width is much wider than the lateral spacing between the firings, the $(i+1)^{st}$ echo is:

$$s_{i+1}(t)=h(t-(Td-T))+h(t-Td)$$

where the first term is in response to the previous firing (i.e., the artifact). If a jitter is introduced to the pulse repetition interval, the $(i+2)^{nd}$ echo is equal to $$s_{i+1}(t)=h(t-(Td-T-\Delta T))+h(t-Td)$$

where the first term is the artifact due to the previous firing.

This difference caused by the jitter acts to shift the artifact where the real signal or information responsive to actual tissue or lack of tissue is not shifted. This distinction may be used to detect, remove, reduce, visualize, or otherwise address the artifact.

The jitter has a period or repeats at a given rate. The variation in PRI caused by the jitter occurs every N pulses where N is 1 or greater. For N=1, the period is two pulses. The jitter is periodic with a periodicity of two firings. The pulse repetition interval alternates between T and $T+\Delta T$ from firing to firing.

The variation may occur less frequently. For example, the variation occurs every second, third or other number of pulses. In one embodiment, the variation occurs between complete scans. The jitter is periodic with a periodicity of two frames. The pulse repetition interval alternates frame to frame. In general, the variation occurs every N frames or volumes where N is 1 or greater. During the scanning of the frame (e.g., two-dimensional region) or volume (three-dimensional region), the PRI is constant between pulses. For different frames or volume scans, the PRI is different, such as X between pulses for frame 1 and X−1 between pulses for frame 2.

The amount of variation or jitter may be set to any level. For example, the amount may be as small as Tc/2, where Tc=1/fc and fc is the imaging center frequency at the deepest depth of an imaging region. The amount of variation is about one half of an inverse of an imaging center frequency associated with the pulses or greater. This variation accounts for actual performance by electronics (design tolerance) and differences due to design choice while providing jitter without visual shift. This amount of jitter with a pattern of alternating every firing may be used to detect and/or reduce the artifact by pre-detection processing of beams from successive firings. The successive firings may be non-collinear for high frame/volume rates.

As another example, a visual or noticeable shift in the artifact is provided by the jitter. The amount of jitter is at least a time corresponding to an axial resolution. Depth is associated with time in pulse-echo imaging. The time for sound to reach an adjacent sample location in the scanned region corresponds to the axial resolution. By varying the PRI by at least a time corresponding to the axial resolution, the artifact in the resulting images shifts by one location or more with the jitter. By being larger than the axial resolution, a visible shift of the artifact occurs. For example a large jitter alternated every frame or every N frames is used to detect or reduce the artifact by post detection processing of frames/volumes, or simply to give the user visual clues (jittering artifact) about the presence of the artifact. By displaying the sequence of image, the jitter causes the artifacts to periodically shift.

The jitter is applied to the pulses for at least one mode of imaging, such as B-mode pulses. The jitter may or may not be applied to other modes. Since interleaving may cause variation in the PRI, the jitter is in addition to variation caused by the interleaving. The variation from the jitter may be more frequent than variation caused by interleaving. Where jitter is applied to pulses for different modes, the same or different jitter is applied.

In act 16, acoustic echoes are received. The echoes are responsive to one or more pulses. Desired echoes or echoes from the scan depths are received in response to a most recent transmit beam. Echoes responsive to an earlier transmit beam from depths beyond the imaging depth (artifacts) are received at a same time. The transducer receives the echoes and converts the echoes into electrical signals. The electrical signals from the different elements are beamformed, such as delayed and summed, to represent echoes from different sample depths along one or more scan lines.

A series of acoustic receive beams are formed. Different beams are received at different times. One or more beams are formed in response to each of the sequential transmissions. Some or all of the receive beams include information from echoes from more than one of the acoustic transmit beams. The extra echoes may be associated with the depth ambiguity artifact.

In act 18, an artifact is detected. Due to the jitter, the artifact may appear at different locations at different times. The varying of the pulse period displaces the artifact. Where the jitter is applied with frame or volume-based period, the displacement occurs between images. By subtracting one image from another, the difference represents the artifact from both images. The difference image is divided into artifact from the two original images for separate removal. If the artifact occurs in a chamber lacking signal, the portion of the difference from the chamber may be removed. In chambers, one of the original images may not have artifacts. The difference image indicates the artifact in the other image.

Where the jitter is applied to different beams in a same frame, the shift of artifact between beams may be detected. Other detection may be used. Filtering or image processing may identify the artifact. The regularly varying jitter causes a periodic shift in the artifact, distinguishing the artifact from other signals. This periodic shift may be used to detect the artifact, such as identifying information that changes with a same period. The shift may be visually detectable or may be small enough that visual detection is not possible. Detection by a processor on data prior to signal or image detection (i.e., prior to removal of phase information by intensity/B-mode detection and/or flow estimation) or any down sampling may be used for shifts less than the axial resolution or for larger shifts.

The presence of the artifact may be detected automatically. Alternatively, the user assists or manually indicates the existence and/or location of the artifact. The detection may be triggered by an event (e.g., a change in image settings), triggered by the user, triggered automatically, triggered at regular intervals (e.g., every few seconds), or performed constantly.

In act 20, the artifact is addressed. The artifact is addressed by warning a user, reduction of the artifact, removal of the artifact, changes in settings associated with the artifact to avoid at least some of the artifact, other alteration affecting the artifact in the current or subsequent imaging, highlighting the artifact by periodical shift, or other reaction to the artifact. Upon detection of the artifact, the user is warned, line duration is increased, or any technique may be employed for automatic artifact reduction.

Changes in settings include altering the pulse repetition interval to avoid the artifact. For example, the PRI is altered to provide no or a weaker artifact. Other settings include the imaging depth, frequency, and power. The imaging depth may be increased or decreased to provide fewer artifacts. The imaging frequency may be increased to increase the rate of attenuation. The power may be decreased to avoid artifact. Settings may be altered iteratively to minimize undesired changes while avoiding or limiting artifact.

In one embodiment, the artifact is reduced and/or removed by filtering in act 22. The filtering is configured to remove information at the jitter frequency. The filtering is applied to data prior to signal detection (e.g., B-mode detection) or to data after signal detection. The filtering is applied regardless of detection of the artifact or in response to detection of the artifact.

Signals responsive to echoes from successive ones of the pulses are filtered. An infinite or finite impulse response filter is applied. The sequential data from different transmit events of the pulse-echo imaging is applied to different taps of the filter, filtering successive ones of the pulses. Where sequential receive beams are along different scan lines, the filtering is lateral filtering along adjacent scan lines.

In one example of filtering, the jitter $\Delta T=Tc/2$. The artifact terms in the adjacent beams are 180 degrees out of phase. A [0.5 0.5] pre-detection filter across firings reduces or eliminates the artifact. Beamformed data is used, but channel data may be filtered. In other embodiments, the beam filter is a longer filter with a zero at half the sampling frequency. Other filters to remove artifact information based on other amounts and/or periods of jitter may be used.

In act 24, an image is generated. The image is generated from the received acoustic echoes. The transduced signals are beamformed, detected or estimated, may be scan converted, and are mapped or used to generate display values. The display values are output to a display as an image.

The image may be associated with an addressed artifact. For example, a warning is output with the image. The warning is visual, audible, or both. As another example, the artifact is reduced or removed, such as by filtering or imaging processing, prior to generation of the image. The filtered or image processed signals are used to generate the image. The resulting image has a less visible or noticeable artifact. In another example, the image includes the artifact without reduction or removal. A sequence of images is shown, but the shift caused by the jitter allows a user to visually distinguish the artifact from other information in the sequence of images. Other approaches to addressing the artifact may be used.

FIG. 8 shows one embodiment of a system for addressing depth ambiguity artifact in ultrasound imaging. The system is an ultrasound imaging system, but other imaging systems may be used. The system includes a transducer 34, a transmit beamformer 32, a receive beamformer 36, a filter 38, an image processor 40, a display 42, and a memory 44. Additional, different, or fewer components may be provided, such as the system including a CINE memory, scan converter, other filters, and/or coherent image former.

The transducer 34 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 34 connects with the transmit beamformer 32 and the receive beamformer 36 through a transmit/receive switch, but separate connections may be used in other embodiments.

The transmit beamformer 32 is a processor, delay, filter, waveform generator, memory, phase rotator, digital-to-analog converter, amplifier, combinations thereof or any other now known or later developed transmit beamformer components. The transmit beamformer 32 is configured as a plurality of channels for generating electrical signals of transmit waveforms for each element of a transmit aperture. The waveforms have relative delay or phasing and amplitude for focusing or defocusing the acoustic energy as a transmit beam. The transmit beamformer 32 includes a controller for altering an aperture (e.g. the number of active elements), an apodization profile across the plurality of channels, a delay profile across the plurality of channels, a phase profile across the plurality of channels, and combinations thereof.

The transmit beamformer 32 generates waveforms for a sequence of transmit beams. The sequence of beams is for imaging in a same mode, such as B-mode pulses. The transmit beamformer 32 may generate interleaved pulses or beams. For example, Doppler and B-mode pulses are interleaved on a line-by-line, group of line-by-group of line, frame-by-frame, or volume-by-volume basis.

For a given mode, the repetition interval between successive beams is jittered or varied. The variation is in addition to variation caused by interleaving pulses of other modes. Jitter other than or different from variation due to interleaving is included in the PRI. The variation is regular, periodic, or otherwise coded to later distinguish the depth ambiguity artifact.

The transmit beamformer 32 varies the pulse period with any rate and by any amount. For example, the transmit beamformer 32 varies the repetition interval by about one half of an inverse of a center frequency of the imaging mode and with a period of about two of the repetition intervals. As another example, the transmit beamformer 32 varies the repetition interval by at least an axial resolution of the image and with a period of at least one or two frame or volume scan periods.

The receive beamformer 36 is a preamplifier, filter, phase rotator, delay, summer, base band filter, processor, buffers, memory, combinations thereof or other now known or later developed receive beamformer components. The receive beamformer 36 is configured into a plurality of channels for receiving electrical signals representing echoes or acoustic energy impinging on the transducer 34. Beamforming parameters including a receive aperture (e.g., the number of elements and which elements are used for receive processing), the apodization profile, a delay profile, a phase profile and combinations thereof are applied to the receive signals for receive beamforming. For example, relative delays and amplitudes or apodization focus the acoustic energy along one or more scan lines. A control processor controls the various beamforming parameters for receive beam formation. The receive beamformer 36 forms beams in response to the transmitted beams.

The filter 38 is a processor, digital signal processor, control processor, application specific integrated circuit, field programmable gate array, digital circuit, analog circuit, combinations thereof, or other filter for filtering data. The filter 38 is positioned prior to the image processor 40 and/or prior to detection of flow or intensity. The filter 38 may be at other locations, such as after the image processor 40, or the filter 38 may not be provided.

The filter 38 filters data responsive to successive ones of the receive beams. Data from adjacent scan lines and/or temporally adjacent receive beams is filtered together. Any number of taps and types of filters may be used. In one embodiment, the filter 38 is a two tap filter with equally weighted taps, providing a zero at half of the sampling frequency. Other spectral responses may be used.

The image processor 40 is a general processor, digital signal processor, control processor, application specific integrated circuit, digital circuit, digital signal processor, analog circuit, B-mode detector, Doppler processor, correlator, combinations thereof, or other now known or later developed processor for envelope detection or motion estimation. The image processor 40 may include filters, scan converters, display mapping tables, buffers, or other components. The image processor 40 generates an image from the beamformed signals.

The image includes the artifact or has had the artifact removed. The artifact in the image may have been reduced or may not be reduced. In one embodiment, the image processor 40 applies an algorithm to detect and address the artifact. In another embodiment, the filter 38 addresses the artifact.

The display 42 is a monitor, LCD, flat panel, plasma, CRT, printer, or other display device. The display 42 provides the image to the user. A sequence of images may be displayed on the display 42. The images may show shift in the artifact.

The memory 44 is a computer readable storage medium having stored therein data representing instructions executable by a programmed processor for reducing or detecting depth ambiguity artifact in ultrasound imaging. The instructions for implementing the processes, methods and/or techniques discussed herein are provided on computer-readable storage media or memories, such as a cache, buffer, RAM, removable media, hard drive or other computer readable storage media. The instructions are implemented on a single device or a plurality of devices in a distributed manner. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for addressing depth ambiguity artifact in ultrasound imaging, the method comprising:
   transmitting a series of pulses from a transducer, the pulses of the series separated in time by a pulse repetition interval;
   periodically varying the pulse repetition interval within the series such that different amounts of time between the pulses increases after about N pulses and decreases after about N pulses;
   receiving acoustic echoes in response to the pulses; and
   addressing the depth ambiguity artifact as a function of the varying
   generating a B-mode image as a function of the received acoustic echoes, the image associated with the depth ambiguity artifact addressed as the function of the varying.

2. The method of claim 1 wherein transmitting the series of pulses comprising forming a series of acoustic transmit beams.

3. The method of claim 2 wherein receiving acoustic echoes comprises receiving for a series of acoustic receive beams, at least some of the acoustic receive beams including echoes from more than one of the acoustic transmit beams.

4. The method of claim 1 wherein periodically varying comprises varying every N pulse where N is 1 or greater.

5. The method of claim 1 wherein periodically varying comprises varying every N frames or volumes, where N is 1 or greater and where the pulse repetition interval is constant between pulses within each frame or volume.

6. The method of claim 5 wherein periodically varying comprises varying by at least a time corresponding to an axial resolution.

7. The method of claim 1 wherein periodically varying comprises varying by one half of an inverse of an imaging center frequency associated with the pulses.

8. The method of claim 1 wherein periodically varying comprises repetitively varying with a period of at least two of the pulses and corresponding pulse repetition intervals.

9. The method of claim 8 wherein repetitively varying comprises varying with the period of about two of the pulses and varying by one half of an inverse of an imaging center frequency associated with the pulses.

10. The method of claim 9 further comprising:
    amplitude detecting from signals responsive to the acoustic echoes from successive ones of the pulses;
    filtering, prior to the amplitude detecting, the signals responsive to the acoustic echoes from the successive ones of the pulses, the successive ones of the pulses being along adjacent scan lines;
    wherein generating the image comprises generating the image with the filtered signals.

11. The method of claim 1 further comprising:
    detecting an artifact displaced as a function of the varying; and
    reducing the artifact, removing the artifact, or changing the pulse repetition interval to avoid the artifact.

12. In a computer readable storage medium having stored therein data representing instructions executable by a programmed processor for addressing depth ambiguity artifact in ultrasound imaging, the storage medium comprising instructions for:
    pulse-echo imaging of an object;
    jittering a pulse period in the pulse-echo imaging; and
    reducing the artifact in the pulse-echo imaging as a function of the jittering.

13. The computer readable storage medium of claim 12 wherein the pulse period is jittered by one half of an inverse of an imaging center frequency and a jitter period is about two pulse repetition intervals of the pulse period.

14. The computer readable storage medium of claim 13 wherein the instructions further comprise:
    amplitude detecting from receive beams responsive to successive firings of the pulse-echo imaging;
    filtering, prior to the amplitude detecting, the receive beams responsive to the successive firings of the pulse-echo imaging.

15. The computer readable storage medium of claim 12 wherein the pulse period is jittered by at least an axial resolution of the pulse-echo imaging and a jitter period is about a frame or volume period of the pulse-echo imaging.

16. A system for addressing depth ambiguity artifact in ultrasound imaging, the system comprising:
    a transmit beamformer configured to transmit beams for a same imaging mode with a repetition interval between successive ones of the beams, the repetition interval regularly varied other than caused by any interleaving between imaging modes;
    a receive beamformer configured to receive beams in response to the transmitted beams; and
    an image processor configured to generate an image from the received beams.

17. The system of claim 16 wherein the transmit beamformer is configured to vary the repetition interval by about one half of an inverse of a center frequency of the imaging mode and with a period of about two times the repetition interval.

18. The system of claim 17 wherein the image processor comprises a B-mode detector configured to detect from data responsive to successive ones of the received beams;
    further comprising a filter configured to filter the data responsive to the successive ones of the received beams prior to detection, the filter having a zero at half a sampling frequency.

19. The system of claim 16 wherein the transmit beamformer is configured to vary the repetition interval by at least an axial resolution of the image and with a period of at least a frame or volume scan period.

20. The system of claim 16 wherein the same imaging mode is B-mode.

* * * * *